US012578327B2

(12) United States Patent
Rabanera et al.

(10) Patent No.: US 12,578,327 B2
(45) Date of Patent: Mar. 17, 2026

(54) STRIP HOLDER

(71) Applicant: DSM AUSTRIA GMBH, Getzersdorf bei Traismauer (AT)

(72) Inventors: Luis Miguel Fidalgo Rabanera, Vienna (AT); Kurt Brunner, Krems (AT); Eva Maria Binder, Tulln (AT); Eva Maria Wanzenböck, Hausleitin (AT); Evangelos Alexiadis, Canterbury (GB); Oliver Bishop, Alton (GB); Andrew Spragg, Ditchling (GB); Ben Childs, Horsham (GB)

(73) Assignee: DSM IP ASSETS B.V., Maastricht (NL)

( * ) Notice: Subject to any disclaimer, the term of this patent is extended or adjusted under 35 U.S.C. 154(b) by 919 days.

(21) Appl. No.: 17/782,280

(22) PCT Filed: Jul. 1, 2020

(86) PCT No.: PCT/EP2020/068564
§ 371 (c)(1),
(2) Date: Jun. 3, 2022

(87) PCT Pub. No.: WO2021/110290
PCT Pub. Date: Jun. 10, 2021

(65) Prior Publication Data
US 2023/0013282 A1 Jan. 19, 2023

(30) Foreign Application Priority Data

Dec. 4, 2019 (EP) ..................................... 19213543

(51) Int. Cl.
| | |
|---|---|
| *G01N 33/53* | (2006.01) |
| *B01L 3/00* | (2006.01) |
| *G01N 25/20* | (2006.01) |

(52) U.S. Cl.
CPC ........ *G01N 33/5302* (2013.01); *B01L 3/5023* (2013.01); *G01N 25/20* (2013.01);
(Continued)

(58) Field of Classification Search
CPC .. G01N 33/5302; G01N 25/20; B01L 3/5023; B01L 2200/0684; B01L 2300/0825
See application file for complete search history.

(56) References Cited

U.S. PATENT DOCUMENTS

| | | | |
|---|---|---|---|
| 9,008,373 B2 | 4/2015 | Markovsky et al. | |
| 2004/0115832 A1 | 6/2004 | Shareef et al. | |
| 2018/0180552 A1* | 6/2018 | Klein ............... | G01N 35/00584 |

FOREIGN PATENT DOCUMENTS

| | | |
|---|---|---|
| CN | 108700579 | 10/2018 |
| CN | 109696544 | 4/2019 |

(Continued)

OTHER PUBLICATIONS

International Search Report for PCT/EP2020/068564 mailed Sep. 22, 2020, 6 pages.
(Continued)

*Primary Examiner* — Dennis White
(74) *Attorney, Agent, or Firm* — NIXON & VANDERHYE P.C.

(57) ABSTRACT

The invention relates to a strip holder consisting of a housing with a front side and a back side, the housing comprising at least one strip receiving channel, at least one fluid receiving channel, at least one fluid reservoir, and optionally at least one ventilation channel. The invention also relates to a use of the strip holder, a method as well as to a kit comprising the strip holder.

20 Claims, 3 Drawing Sheets

(52) U.S. Cl.
CPC .................. *B01L 2200/0684* (2013.01); *B01L 2300/0825* (2013.01)

(56) References Cited

FOREIGN PATENT DOCUMENTS

| EP | 1 102 066 | 5/2001 |
| EP | 1 686 378 | 8/2006 |
| WO | 02/093169 | 11/2002 |
| WO | 2009/038798 | 3/2009 |
| WO | WO 2013/182491 | 12/2013 |
| WO | 2018/125271 | 7/2018 |

OTHER PUBLICATIONS

Written Opinion of the ISA for PCT/EP2020/068564 mailed Sep. 22, 2020, 7 pages.
Koczula et al., "Lateral flow assays", Essays Biochem, vol. 60, issue 1, Jun. 2016, one (1) page.
Krska et al., "Rapid test strips for analysis of mycotoxins in food and feed", Analytical and Bioanalytical Chemistry, 393, pp. 67-71, 2009—published Oct. 21, 2008, one (1) page.

* cited by examiner

STRIP HOLDER

This application is the U.S. national phase of International Application No. PCT/EP2020/068564 filed Jul. 1, 2020 which designated the U.S. and claims priority to EP 19213543.2 filed Dec. 4, 2019, the entire contents of each of which are hereby incorporated by reference.

The present invention relates to a strip holder consisting of a housing with a front side and a back side, wherein the housing comprises at least one strip receiving channel, at least one fluid receiving channel, and at least one fluid reservoir, wherein the at least one strip receiving channel and the at least one fluid receiving channel are in fluid connection with the at least one fluid reservoir, and wherein the front side is made of a solid material and comprises at least one inspection window. The present invention further relates to a use of the strip holder, as well as a kit comprising the strip holder.

Rapid and reliable detection of analytes is a crucial requirement in numerous and diverse areas. Lateral flow immunoassays, also referred to as lateral flow immunochromatographic assays or lateral flow tests, are an easy-to-use tool to evaluate the presence or absence and in some cases also the quantity of an analyte-of-interest in a sample.

The basic principle of lateral flow tests is well-known in the art. Typically, a lateral flow test strip is a membrane-based carrier, which comprises at least a sample loading zone, a conjugate pad and a test zone. The conjugate pad comprises labeled binding agents, often labeled antibodies, which can bind specifically to an analyte-of-interest. The test zone comprises immobilized un-labeled binding agents, which can also bind specifically the analyte-of-interest. When a sample fluid is contacted with the sample loading zone of the lateral flow test strip, the sample fluid traverses the strip by capillary flow. First, the sample fluid migrates to the conjugate pad. In case the sample fluid contains the analyte-of-interest, the analyte is bound by the labeled binding agents. The sample fluid migrates further to the test zone, where the analytes bound by the labeled binding agents of the conjugate pad are bound by the immobilized un-labeled binding agents. Hereby, analytes provide a connection of the labeled binding agents to the immobilized un-labeled binding agents, thus facilitating an accumulation of the label in the test zone. Often, a lateral flow test strip further comprises a control zone, comprising immobilized un-labeled binding agents which can bind the labeled binding agents. Excess labeled binding agents from the conjugate pad, which are not bound in the test zone, are hereby bound in the control zone, providing a positive control for successful mobilization and functionality of the labeled binding agents. Via detection of the label in the test zone, a conclusion on the presence or absence of the analyte in the sample fluid can be drawn. Examples of lateral flow tests are disclosed e.g. in Koczula and Gallotta. Essays Biochem. 2016 Jun. 30; 60(1):111-20 or in Krska and Molinelli. Anal Bioanal Chem, 2009 January; 393(1):67-71.

The binding agents of a lateral flow test strip can be adapted to specifically bind to a large number of different analytes. Hereby, lateral flow tests offer very broad applicability and are routinely used in many fields such as environmental testing, evaluation assays of human, animal and plant health, food and feed testing etc. Lateral flow tests are performed not only by technical professionals in laboratory use but also by untrained personnel and individuals, e.g. in home testings, point-of-care testings etc.

In its simplest form, a lateral flow test can be performed using solely a test strip and a sample fluid. However, to improve handling, to optimize assay conditions or to exclude incorrect or non-intended operation by a user, more advanced lateral flow test setups can be provided. Especially in cases where a user is expected to be a non-trained person, as e.g. in pregnancy tests, strip holders or casings can provide features of convenience such as protection of the test strip or the sample, and operating guidance for the intended user.

In order to achieve maximum reproducibility and comparability between two or more lateral flow test results, it is imperative for the tests to be conducted under comparable—ideally identical—conditions. However, since lateral flow tests are performed not only in temperature-controlled laboratories but frequently in the field or in non-regulated premises all over the world, temperature differences have a considerable undesirable impact on reproducibility and comparability.

Another factor to be considered in terms of reproducibility is human error or lack of equipment. In particular, the application of a sample onto the lateral flow test strip at an optimal volume and at the correct section of the strip can pose a challenge for non-trained users and/or persons lacking laboratory equipment such as precision pipettes. As a consequence, either too little sample is loaded onto the test strip, resulting in a lack of liquid as mobile phase in the chromatographic assay. Or too much sample is loaded onto the test strip, resulting in strip drowning and in the case of typical strip holders in strip holder flooding. In addition, reproducibility and comparability are further negatively affected by varying sample volumes being applied to the test strip. There is thus a need for a solution to facilitate reproducible application of sample fluid to a lateral flow test strip while avoiding strip drowning or holder flooding.

Examples for strip holders can be found in literature, e.g. in the form of a cartridge assembly as described in WO 2018/125271 A1. The cartridge assembly disclosed in WO 2018/125271 A1 comprises at least a base portion and a removably connected cap portion, wherein a flange of the base portion has to be disposed in the cap portion to allow forming of a fluid-flow passage. In such a cartridge assembly, fluid can be introduced into the base portion, which fluid is guided further into the cap portion via a fluid-flow passage of the flange of the cap portion and an optional additional fluid filter structure to ultimately arrive in a fluid receiving void of the cap portion where the fluid may contact a test strip. While such a cartridge assembly setup can be expected to be well-suited for certain assays and might even be transferred e.g. in an incubator oven to achieve a controlled temperature, the specific arrangement of the individual components required for the disclosed cartridge assembly would not allow fast, efficient and even heat transfer from an external temperature source to the test strip and the sample fluid inside the cartridge assembly. Also, the cartridge assembly of WO 2018/125271 A1 lacks solutions to deal with mistakenly added excess fluid. Other examples may be in the form of an insert cassette for an assay reader as described in WO 2009/038798, or as module part of a reader apparatus as described in U.S. Pat. No. 9,008,373 B2.

In EP 1 102 066 A2, US 2004/0115832 A1 and WO 02/093169, strip holders are described wherein a strip is enclosed in a receiving well within a plastic strip holder casing or cassette, consisting of a top element and a bottom element, which elements are mated to form the casing. A sample fluid may be applied onto such an enclosed strip via an application port. To achieve temperature transfer from the outside to the enclosed strip, a bar or plate element is described to contact the strip, which bar or plate element is made of a different material than the plastic strip holder casing or cassette. In particular, the bar or plate element is described to be made of a metal such as copper, gold, silver, aluminum or metal alloys. Such strip holders are designed for single-use only and cannot be re-used due to the irreversible enclosure of the strip inside the casing.

In summary, despite the existence of some types and embodiments of strip holders, suitable technical solutions to improve reproducibility and comparability of lateral flow assays are still needed. The present invention therefore aims at providing a strip holder that allows performing lateral flow assays in a reproducible and comparable manner by providing a solution to non-regulated ambient temperatures.

To solve this objective, a strip holder according to the present invention is essentially characterized in that the back side of the housing is an essentially flat surface; wherein the back side of the housing is thermally conductive. This embodiment allows conducting lateral flow assays at operator-defined temperatures via the essentially flat back side of the housing which can be contacted with a thermal element, namely a heating or cooling device that determines the temperature at which the assay is performed. By providing a strip holder having a back side, which outer surface provides for close contact with a thermal element and rapid transfer from the thermal element into the strip holder, it is possible to maintain or hold not only one strip holder but a plurality of strip holders over time at a defined temperature, which allows mitigation or even elimination of poor reproducibility, reliability or comparability of lateral flow assay results caused by temperature variability. Even in case such a strip holder is not contacted with a thermal element directly but e.g. solely transferred into an incubator oven, the essentially flat and thermally conductive back side ensures an even and fast temperature transfer of the outside temperature onto the test strip inside the strip holder.

Any channel structure that can accommodate a typical lateral flow assay strip can be a strip receiving channel. Any channel structure that allows a flow of liquids from one opening of the channel to the other can be a fluid receiving channel. Herein, the terms "liquid" and "fluid" are used interchangeably. In one embodiment of the invention, the fluid receiving channel is the same channel structure as the strip receiving channel. For the avoidance of doubt, the phrase "in fluid connection" as used herein means that a fluid may pass from one component to the other. For instance, when a channel and a reservoir are in fluid connection, it is possible to pour a fluid through the channel into the reservoir.

Any structure that is in fluid connection with a fluid receiving channel and that can hold a defined amount of liquid in a strip holder can be a fluid reservoir. A fluid reservoir can have the same, smaller or larger width dimensions as/than a fluid receiving channel.

An inspection window as referred to herein, is a structure that allows viewing of at least one test strip inserted into a strip holder from the outside, in particular viewing of the test zone, and the additional control zone of the test strip if available. An inspection window can be a recess or a cut-out or an opening in the housing, through which the test zone and the optionally available control zone on a test strip inserted into a strip holder can be inspected. An inspection window can also be implemented by using a see-through material on the strip holder housing, such as transparent foil materials or glass:

Herein, a surface is considered an essentially flat surface when no surface irregularities are observable on a macroscopic scale, i.e. no surface irregularities can be observed with the naked eye.

A thermally conductive back side as referred to herein, can be defined by its specific heat transfer index. A thermally conductive back side can be any back side with a specific heat transfer index of at least $0.0167 \text{ s}^{-1}$, preferably of at least $0.02 \text{ s}^{-1}$, preferably of at least $0.03 \text{ s}^{-1}$, more preferably of at least $0.05 \text{ s}^{-1}$, more preferably of at least $0.075 \text{ s}^{-1}$, most preferably of at least $0.08 \text{ s}^{-1}$. The specific heat transfer index of a back side can be determined experimentally by calculating the reciprocal of the time in seconds required to achieve a temperature transfer of 10° C. from 25° C. to 35° C. from the outside of the back side of a strip holder housing to the inside of the back side of the strip holder housing. Preferably, the thickness of the back side of the strip holder is between 0.001 and 1.5 mm, more preferably between 0.001 and 1.2 mm, even more preferably between 0.01 and 1 mm, even more preferably between 0.015 and 0.8 mm, most preferably between 0.03 and 0.7 mm. A person skilled in the art is aware of the fact that the specific heat transfer index of a back side of a strip holder depends on the material as well as on the thickness of the back side.

To serve merely as an example, if a temperature transfer from 25° C. to 35° C. was achieved in 5.8 seconds by a back side made of a first material at a thickness of 1 mm, and in 10 seconds by a back side made of the same material at a thickness of 2 mm, and the same temperature transfer from 25° C. to 35° C. was achieved in 4 seconds by a back side made of a second material at a thickness of 0.2 mm, the specific heat transfer indices of these three back sides would be $1/5.8=0.172 \text{ s}^{-1}$, $1/10=0.100 \text{ s}^{-1}$, and $1/4=0.250 \text{ s}^{-1}$, respectively.

Practically, the specific heat transfer index of a certain back side of a strip holder shall be determined by placing a thermometer inside of a strip holder with the back side to be tested, and placing said strip holder onto a thermal element. Such a thermal element is essentially a surface that can be hold at a chosen temperature, such as one from a laboratory hotplate, whereby the back side of the strip holder contacts the hotplate surface. The temperature in the inside of the strip holder is measured at regular time points as soon as the strip holder is contacted with the hotplate surface. Hereby, the data required to calculate the specific heat transfer index can be collected. To this end, a laboratory hotplate is set to 45° C. and the strip holder with the back side to be tested is contacted with this hotplate as described above. Starting from typical room temperature, herein defined as any temperature between 18° C. and 25° C., preferably between 22° C. and 24° C., the rise in temperature in the inside of the strip holder is followed and used to calculate the specific heat transfer index as described above. The specific heat transfer index is to be determined by calculating the reciprocal of the time in seconds required to achieve a temperature transfer of 10° C. from 25° C. to 35° C. from the outside of the back side of a strip holder housing to the inside of the back side of the strip holder housing when performing an experiment as described above.

Due to a lack of suitable equipment or technical expertise or simply due to human error, inappropriate amounts of sample liquid may be applied to a test strip. As a consequence, either the amount of sample and/or buffer is insufficient, or strip drowning or strip holder flooding may occur. Therefore, as one embodiment of the invention, a strip holder is provided, consisting of a housing with a front side and a back side, wherein the housing comprises at least one strip receiving channel, at least one fluid receiving channel, and at least one fluid reservoir, wherein the at least one strip receiving channel and the at least one fluid receiving channel are in fluid connection with the at least one fluid reservoir; wherein the front side is made of a solid material and comprises at least one inspection window; wherein the at least one, fluid reservoir is partly separated by at least one strip supporting structure comprising at least one weir structure; wherein the at least one strip supporting structure is provided below the at least one strip receiving channel and the at least one fluid receiving channel; and wherein the at least one strip supporting structure is provided in orthogonal orientation to the at least one strip receiving channel and the at least one fluid receiving channel.

The at least one strip supporting structure comprising at least one weir structure defines a first sub-reservoir of the partly separated at least one fluid reservoir. The first sub-reservoir forms a bin or well designed to hold a predefined liquid volume of 50 to 5000 µL. More preferably, the first sub-reservoir is designed to hold a liquid volume of 100 to 500 µL, even more preferably of 100 to 300 µL, most preferably of 150 to 250 µL. A liquid held in the first sub-reservoir has preferably a depth of 2 to 7 mm. A liquid volume exceeding the maximal volume of the first sub-reservoir may flow over the at least one weir structure into a second sub-reservoir of the partly separated at least one fluid reservoir. The second sub-reservoir is preferably designed to hold a liquid volume of at least 50 µL, preferably of at least 100 µL, more preferably of at least 200 µL, even more preferably of at least 250 µL.

By providing a strip holder consisting of a housing with a front side and a back side, characterized in that the housing comprises at least one strip receiving channel, at least one fluid receiving channel, and at least one fluid reservoir, wherein the at least one strip receiving channel and the at least one fluid receiving channel are in fluid connection with the at least one fluid reservoir; wherein the front side is made of a solid material and comprises at least one inspection window; wherein the back side of the housing is an essentially flat surface; wherein the back side of the housing is thermally conductive; wherein the at least one fluid reservoir is partly separated by at least one strip supporting structure comprising at least one weir structure defining a sub-reservoir capable of holding a predefined fluid volume, wherein the at least one strip supporting structure is provided below the at least one strip receiving channel and the at least one fluid receiving channel; and wherein the at least one strip supporting structure is provided in orthogonal orientation to the at least one strip receiving channel and the at least one fluid receiving channel, a strip holder is provided that allows conducting lateral flow assays at operator-defined temperature(s) and that allows a minimization of the risks of applying non-appropriate amounts of sample liquid. Such a strip holder allows performing lateral flow assays in a reproducible and comparable manner.

According to the invention, a strip holder as described herein is provided, wherein the at least one strip receiving channel and the at least one fluid receiving channel are provided as separate channels. In particular, a strip holder as described herein is provided, wherein the at least one strip receiving channel and the at least one fluid receiving channel are provided in parallel orientation to one another. The at least one strip receiving channel and the at least one fluid receiving channel comprised by a strip holder as described herein are provided in a way, wherein the at least one strip receiving channel and the at least one fluid receiving channel have an open top end. An open top end as referred to herein is an opening of the channel opposite to another opening at the fluid reservoir. Hereby, handling of a lateral flow assay can be achieved most conveniently, insofar as that a test strip can be inserted into the strip holder first and the sample liquid can be added in a second step via the distinct fluid receiving channel, thus avoiding premature contacting of the sample with the test strip and thus premature initiation of the assay reaction. Also, by providing a strip receiving channel having an open top end, it becomes possible to remove a test strip from the strip holder after performing the assay, and to insert another test strip into the strip holder. Hereby, the same sample liquid could be tested subsequently with two different test strips. Alternatively, the strip holder could be rinsed and re-used with another test strip and another sample liquid.

Typical channel structures in strip holders are designed to occupy as little space as possible to achieve an overall small and convenient format of the strip holder. However, when applying strip and sample fluid, air inside the strip holder builds up back pressure, resulting in undesirable or dysfunctional liquid flow in the strip holder. By providing a strip holder as described herein, wherein the housing further comprises a ventilation channel, which ventilation channel comprises two openings, wherein a first opening is provided at the at least one fluid reservoir, and a second opening is provided at a level above a fluid reservoir, preferably substantially at a level of an insertion opening of the least one strip receiving channel, a separate escape route for air is provided, back pressure build-up can be avoided and applied sample liquid can flow through the strip holder as intended and without hindrance by back pressure. Any channel structure that allows unblocked passage of air or comparable gases from one opening of the channel to the other and that allows exiting of such gases from inside a strip holder to the outside can be a ventilation channel.

In a preferred embodiment of the invention, a strip holder is provided, wherein the ventilation channel is provided to surround at least partly the at least one fluid reservoir. Hereby, the risk of spilling of liquids into the ventilation channel and thus blockage thereof can be minimized or even avoided altogether.

Many strip holders nowadays are assembled from several individual pieces. However, multi-piece strip holders are more complicated in production. Also, every assembly junction bears a risk of leakage and instability. It is therefore a further objective of this invention to provide a strip holder that consists of as few pieces as possible. By providing a strip holder as described herein, wherein the front side of the housing, the at least one strip receiving channel, the at least one fluid receiving channel, the at least one fluid reservoir, and the at least one ventilation channel are provided as a single piece, a strip holder can be obtained that has a minimum amount of assembly junctions. Hereby, production and assembly are less complicated, and stability and leakproofness are improved. The front side of the strip holder housing, the at least one strip receiving channel, the at least one fluid receiving channel, the at least one fluid reservoir, and the at least one ventilation channel can be formed from any material suitable for injection molding.

The present invention further relates to a strip holder as described herein, wherein the front side of the housing, the at least one strip receiving channel, the at least one fluid receiving channel, the at least one fluid reservoir, the back side of the housing, and the at least one ventilation channel are provided as a single piece, i.e. as a whole. Such a strip holder can be produced as a single piece, wherein the front side and the back side of the housing are connected on the longer or on the shorter side. Such a single piece strip holder can be assembled e.g. by folding the front side and the back side towards each other and connecting them, e.g. by glue-ing, heat-sealing or hot-melting, thus sealing the housing. By providing the strip holder as a single piece, it becomes possible to provide the back side with a smaller thickness than the front side. Thereby, a sufficiently efficient heat transfer can be achieved from the outside via the back side to a strip contained in such a strip holder without a risk for damaging the back side during production or use.

To facilitate efficient temperature transfer from outside the strip holder to the inside, a strip holder is provided, wherein the back side of the housing is made of at least one of the materials selected from the group of aluminum, copper, nickel, tin, silver, gold, polyethylene, polypropyl-ene, polyvinylchloride, polystyrene, polyester, polycarbon-ate, acrylonitrile butadiene styrene (ABS) or ABS-like mate-rial, preferably of the materials selected from the group of polyethylene, polypropylene, aluminum and acrylonitrile butadiene styrene (ABS) or ABS-like material, according to a further embodiment of the invention. By using these materials, the back side of the strip holder housing can be provided in a way that allows transfer of a temperature outside the strip holder to the strip holder inside sufficiently fast to result in an even temperature distribution and stable assay conditions and thus improved comparability. In an embodiment, a strip holder as described herein is provided, wherein the back side of the housing is made of at least one of the materials selected from the group of polyethylene, polypropylene, polyvinylchloride, polystyrene, polyester, polycarbonate, acrylonitrile butadiene styrene co-polymer (ABS) or ABS-like material. In another embodiment, the back side of the housing is made of at least one of the materials selected from the group of polyethylene, polypro-pylene, polyvinylchloride, polystyrene, polyester, polycar-bonate, acrylonitrile butadiene styrene co-polymer (ABS) or ABS-like material; and the back side has a thickness of at most 1 mm, such as at most 0.5 mm, such as at most 0.1 mm, such as at most 40 μm, such as at most 8 μm. In a further embodiment, the back side of such a strip holder has a specific heat transfer index of at least 0.0167 s$^{-1}$, such as at least 0.02 s$^{-1}$, such as at least 0.03 s$^{-1}$, such as at least 0.05 s$^{-1}$, such as at least 0.075 s$^{-1}$, such as at least 0.08 s$^{-1}$. Despite the prevalent dogma and reservations in the state-of-the-art that plastics cannot be suitable materials to allow efficient heat transfer from the outside to a strip contained in a strip holder, as emphasized e.g. in EP 1 102 066 A2 or in WO 02/093169, it was unexpectedly found that a strip holder as described herein, wherein the back side of the housing is made of a plastic material as described above, is perfectly suitable to allow efficient heat transfer. Hereby, a strip holder can be provided which is made entirely of the same plastic material and thus does not need to be combined with a separate metal element, saving costs and allowing a rapid production.

A further obstacle in terms of reproducibility is the exact position of the test strip inside the strip holder after insertion of the test strip. On the one hand, a strip receiving channel needs to be sufficiently wide to allow smooth insertion of the test strip into the strip holder. On the other hand, a strip receiving channel needs to provide sufficient support of the inserted test strip to limit the range of free movement of the test strip and to keep the test strip in a fixed position once inserted. To achieve this goal, a strip holder is provided, wherein the strip receiving channel further comprises at least one wedge-shaped element, wherein the at least one wedge-shaped element is provided on the inside of the front side of the strip holder housing. Hereby, the cross-section of the strip receiving channel is partly reduced by the presence of the wedge-shaped element, thus reducing the risk of an operator inserting the test strip in the wrong orientation. A strip is inserted in the right orientation when the sample loading zone is positioned in the fluid reservoir and the test zone of the lateral flow assay test strip is visible through the inspection window. Also, the inserted test strip is hereby pressed against the inside of the back side of the housing, thus locking the test strip in a fixed position as well as reducing a temperature-isolating air gap between the back side of the housing and the test strip.

Most reproducible and convenient evaluation of lateral flow assay data can be achieved by imaging of the test and optional control zones on the strip by a camera, e.g. installed in a reader apparatus. To allow this approach, the test strip inserted into a strip holder has to be visible to the camera, e.g. through an inspection window. By providing a strip holder as described herein, wherein the lateral walls of the inspection window of the at least one strip receiving channel are beveled, imaging quality can be optimized since the lateral walls do not cast shadows on the test strip, and light reflection into the camera while imaging is minimized or even completely avoided.

To achieve this effect, the bevel is provided in a way that the inspection window gets wider from the inside to the outside of the strip holder housing. The lateral walls of the inspection window are beveled at least at an angle between 1 and 75 degrees, preferably at an angle between 15 and 75 degrees, more preferably at an angle between 35 and 55 degrees, most preferably at an angle between 40 and 50 degrees.

Yet another risk for negatively impacting handling con-venience can be the lack of a suitable structure to allow filling of sample fluid into the fluid receiving channel. By providing a strip holder as described above, wherein the at least one fluid receiving channel is further provided with at least one funnel at an opening of the at least one fluid receiving channel opposite to an opening at the fluid reser-voir, convenient transfer of a sample fluid into the strip holder can be facilitated. In other words, the at least one funnel is provided as an extension of the open top end of the at least one fluid receiving channel.

This goal can be achieved in an even more efficient manner by optimizing the structure of the funnel. In a preferred embodiment of the invention, a strip holder is therefore provided, wherein the at least one funnel is pro-vided with at least two differently beveled inner surfaces. Hereby, the flow of a sample fluid can be directed into the fluid receiving channel independent from the exact location where the sample fluid is transferred into the funnel.

To optimize the overall procedure of a lateral flow assay and to minimize the need for human input, the structure of nowadays' strip holders may be designed to fit into a reader or evaluation apparatus. However, when designing a strip holder to fit into a corresponding reader apparatus, an objective is to provide the strip holder in a manner that still allows convenient addition of sample fluid and to avoid too deep insertion of the strip holder into the reader apparatus. To solve this problem, a strip holder is herein provided, wherein an outside surface of the at least one funnel is inclined at a different angle than the outside surface of the back side of the housing, wherein said outside surface of the at least one funnel defines a stop limiting the insertion depth of the strip holder into an evaluation apparatus. Hereby fluids can be easily transferred into the strip holder, even though the strip holder is already inserted into the reader apparatus.

The invention is further directed to a use of a strip holder in a lateral flow assay at an operator-defined temperature in an evaluation apparatus comprising a heating and/or cooling module, wherein the heating and/or cooling module is set to a temperature at which the lateral flow assay shall be conducted; a lateral flow test strip is inserted into a strip holder as described herein; the strip holder is inserted into the evaluation apparatus, wherein the back side of the strip holder is brought in contact with the heating and/or cooling module; optionally, the strip holder is incubated for a predefined time, preferably for at least 5 seconds; a fluid comprising an analyte to be detected is added into the strip holder; and wherein the strip holder containing the lateral flow test strip and the fluid is incubated for a predefined time, preferably for at least one second, more preferably for at least three seconds, most preferably for at least five seconds. It is apparent to a person having skill in the art that the steps of the use described herein do not have to be performed in the particular order in which they are described above to perform the invention. For instance, the step of adding a fluid comprising an analyte to be detected into the strip holder could be performed before inserting the strip holder into the evaluation apparatus. A person skilled in the art is capable of considering the orders of the steps of the lateral flow assay described herein that allow performing the invention. Preferably, the use relates to a use of a strip holder in a lateral flow assay at an operator-defined temperature in an evaluation apparatus, wherein the evaluation apparatus comprises a heating and/or cooling module, and wherein the lateral flow assay comprises the steps of 1.) setting the heating and/or cooling module to a temperature at which the lateral flow assay shall be conducted; 2.) inserting a lateral flow test strip into a strip holder as described herein; 3.) inserting the strip holder into the evaluation apparatus, wherein the back side of the strip holder is brought in contact with the heating and/or cooling module; 5.) adding a fluid comprising an analyte to be detected into the strip holder; 6.) incubating the strip holder containing the lateral flow test strip and the fluid for a predefined time, preferably for at least one second, more preferably for at least three seconds, most preferably for at least five seconds; and wherein the steps are performed in ascending order from 1.) to 6.). In a particularly preferred embodiment, the lateral flow assay further comprises a further step 4.) incubating the strip holder for a predefined time, preferably for at least 5 seconds. By using a strip holder as disclosed above, it becomes possible to obtain comparable and reproducible lateral flow assay results at a temperature which can be defined by the operator and which is independent from external temperature conditions.

Another aspect of the invention relates to a method for performing a lateral flow assay at an operator-defined temperature in an evaluation apparatus comprising a heating and/or cooling module, wherein the heating and/or cooling module is set to a temperature at which the lateral flow assay shall be conducted; a lateral flow test strip is inserted into a strip holder as described herein; the strip holder is inserted into the evaluation apparatus, wherein the back side of the strip holder is brought in contact with the heating and/or cooling module; optionally, the strip holder is incubated for a predefined time, preferably for at least 5 seconds; a fluid comprising an analyte to be detected is added into the strip holder; and wherein the strip holder containing the lateral flow test strip and the fluid is incubated for a predefined time, preferably for at least one second, more preferably for at least three seconds, most preferably for at least five seconds. Preferably, the invention relates to a method for performing a lateral flow assay at an operator-defined temperature in an evaluation apparatus, wherein the evaluation apparatus comprises a heating and/or cooling module, and wherein the lateral flow assay comprises the steps of 1.) setting the heating and/or cooling module to a temperature at which the lateral flow assay shall be conducted; 2.) inserting a lateral flow test strip into a strip holder as described herein; 3.) inserting the strip holder into the evaluation apparatus, wherein the back side of the strip holder is brought in contact with the heating and/or cooling module; 4.) optionally incubating the strip holder for a predefined time, preferably for at least 5 seconds; 5.) adding a fluid comprising an analyte to be detected into the strip holder; 6.) incubating the strip holder containing the lateral flow test strip and the fluid for a predefined time, preferably for at least one second, more preferably for at least three seconds, most preferably for at least five seconds; and wherein the steps are performed in ascending order from 1.) to 6.).

An evaluation apparatus as referred to herein can be any apparatus or device suitable for supporting the steps of a lateral flow assay including e.g. imaging or recording as well as analyzing of the data obtained from the assay. A heating and/or cooling module as referred to herein comprises at least one essentially flat surface of its own which can contact the essentially flat surface of the back side of a strip holder housing. When in contact, minimization of air gaps between the heating and/or cooling module and the strip holder back side is seeked to allow fast as well as uniform temperature transfer. The step of analyzing the lateral flow assay refers at least to imaging of the test strip. Optionally, further automated data evaluation by analysis and interpretation of the recorded image(s) may be additionally performed.

Best lateral flow assay results can be achieved when the individual components are designed in a way that they comply with one another and structural obstructions are avoided. Therefore, the invention further relates to a kit comprising at least one strip holder as described above, at least one lateral flow assay strip and an evaluation apparatus, wherein the evaluation apparatus is capable of receiving the at least one strip holder and wherein the evaluation apparatus comprises a temperature control element. By providing the necessary components as a kit as described herein, it becomes possible to guarantee optimal matching and complementarity of the components with one another and thus to achieve optimized assay conditions and assay reproducibility. A temperature control element can be e.g. a heating or cooling element. Preferably, the temperature control element is provided in the evaluation apparatus in a manner that allows close contact of the temperature control element to the at least one strip holder. An aspect of the invention therefore relates to an evaluation apparatus, wherein the evaluation apparatus is capable of receiving the at least one strip holder as described herein, and wherein the evaluation apparatus comprises a temperature control element. In a preferred aspect of the invention, the evaluation apparatus comprises at least one insertion slot for receiving the at least one strip holder as described herein, wherein the temperature control element is provided to contact at least 20%, preferably at least 30%, more preferably at least 40% of the back side of the at least one strip holder once the at least one strip holder is inserted into the at least one insertion slot. Hereby, a temperature transfer can be achieved most efficiently from the temperature control element to the strip holder according to the present invention. More preferably, the evaluation apparatus further comprises a camera, wherein the camera is provided to allow imaging of a test strip inside the strip holder through the inspection window. Even more preferably, the evaluation apparatus further comprises a transparent plane, preferably a glass plane, which transparent plane separates the camera from the at least one strip holder. Hereby, the risk of spillings onto the camera can be minimized while still allowing imaging of lateral flow test strips. Even more preferably, the evaluation apparatus further comprises a code reader slot. A code reader slot as referred to herein can be a slot for inserting any kind of code-bearing device, e.g. a card bearing a matrix barcode code or a linear barcode. Preferably, the code reader slot is provided to allow reading of the code by the camera of the evaluation apparatus.

In the following, the solution of the present invention is further described by figures and examples.

DETAILED DESCRIPTION

Figure 1:
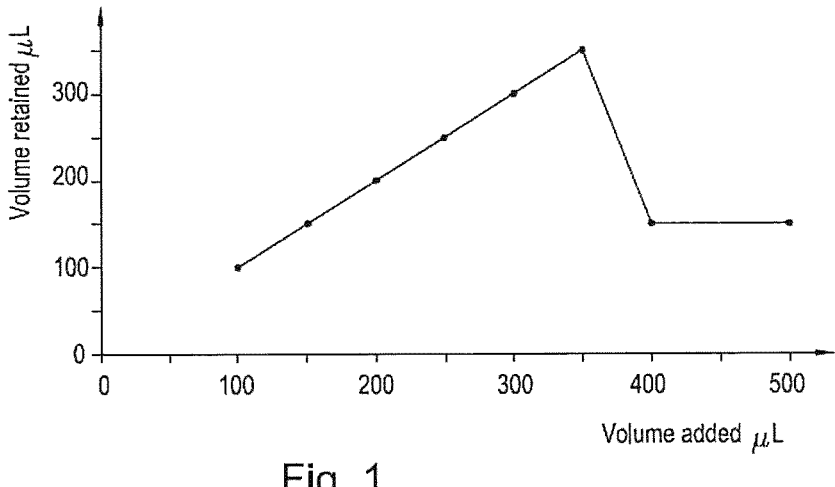
FIG. 1 is a graph showing the relation of volume of liquid retained in a sub-reservoir in a strip holder to the volume of liquid added into the strip holder.

FIG. 1 is a graph demonstrating the functionality provided by a sub-reservoir defined by a strip supporting structure comprising a weir structure within the fluid reservoir of a strip holder. In the graph, the x-axis shows the volume in μL introduced into the strip holder, the y-axis shows the volume in μL that was retained in the sub-reservoir. The nominal geometrical volume defined by the sub-reservoir defined by a strip supporting structure comprising a weir structure was 250 μL. Due to water surface tension also volumes higher than the nominal geometrical volume of the first sub-reservoir were retained. However, these volumes did not result in strip drowning. Volumes higher than 350 μL flowed over the weir structure into the fluid reservoir underneath the sub-reservoir, thus avoiding strip drowning and strip holder flooding. Hereby, strip drowning upon addition of excess volume could be avoided while still retaining a suitable volume that allows performing a reliable lateral flow assay.

Figure 2:
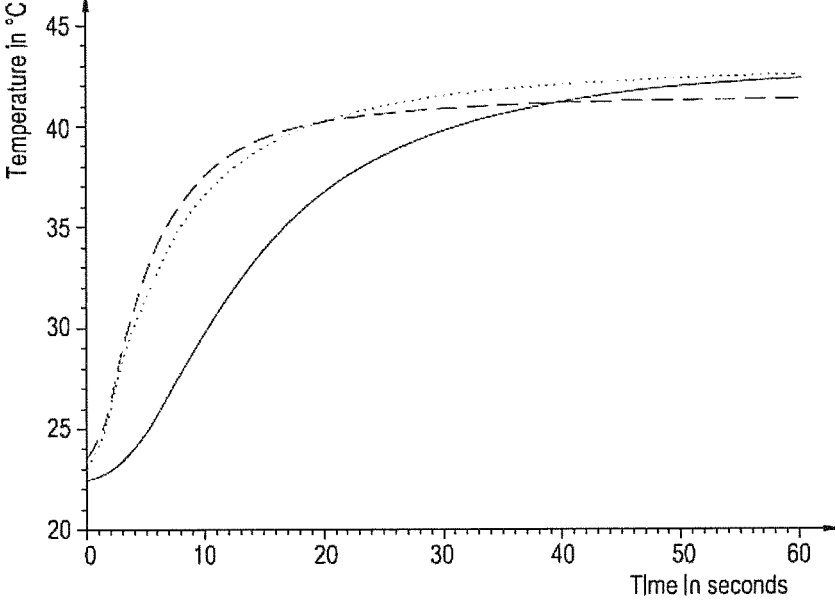
FIG. 2 is a graph showing heat transfer curves of strip holders with three different back sides.

FIG. 2 is a graph showing the heat transfer behavior of different example strip holder back sides. The x-axis shows the time in seconds, and the y-axis shows the measured temperature in $^\circ$ C. The dotted line represents the data recorded when using a strip holder with a back side A (50 μm polyolefin film with 50 μm inert encapsulated silicone adhesive). The dashed line represents the data recorded when using a strip holder with a back side B (38 μm non-permeable soft aluminum foil). The solid line represents the data recorded when using the strip holder with a back side C (0.5 mm acrylonitrile butadiene styrene-like plastic foil). All tested back side materials have a specific heat transfer index of more than $0.08 \ s^{-1}$ and were thus found suitable to allow efficient heat transfer from an external heating/cooling source into the strip holder. Hereby, independence from ambient temperature can be achieved and lateral flow assays can be performed at an operator-defined temperature and thus in a more reproducible and reliable manner.

In the following, exemplary embodiments of strip holders according to the present invention are described in detail. These embodiments serve merely as illustrative examples and are not to be construed as limiting embodiments of the present invention. In the FIGS. 3-12, the reference signs are used consistently for the indicated features. For instance, the feature "a strip receiving channel" is indicated with reference sign 2. Consequently, in the FIGS. 3-12, the reference sign 2 always indicates the feature "a strip receiving channel". In FIGS. 3-12, shown strip receiving channels 2 or fluid receiving channels 3 have an open end located essentially at the top of the strip holder. In particular, these channels are provided in a way to allow insertion of a strip or of a fluid into a strip receiving channel 2 or a fluid receiving channel 3, respectively, from the top end of the strip holder 100.

Figures 3, 4, 5, 6, 7:
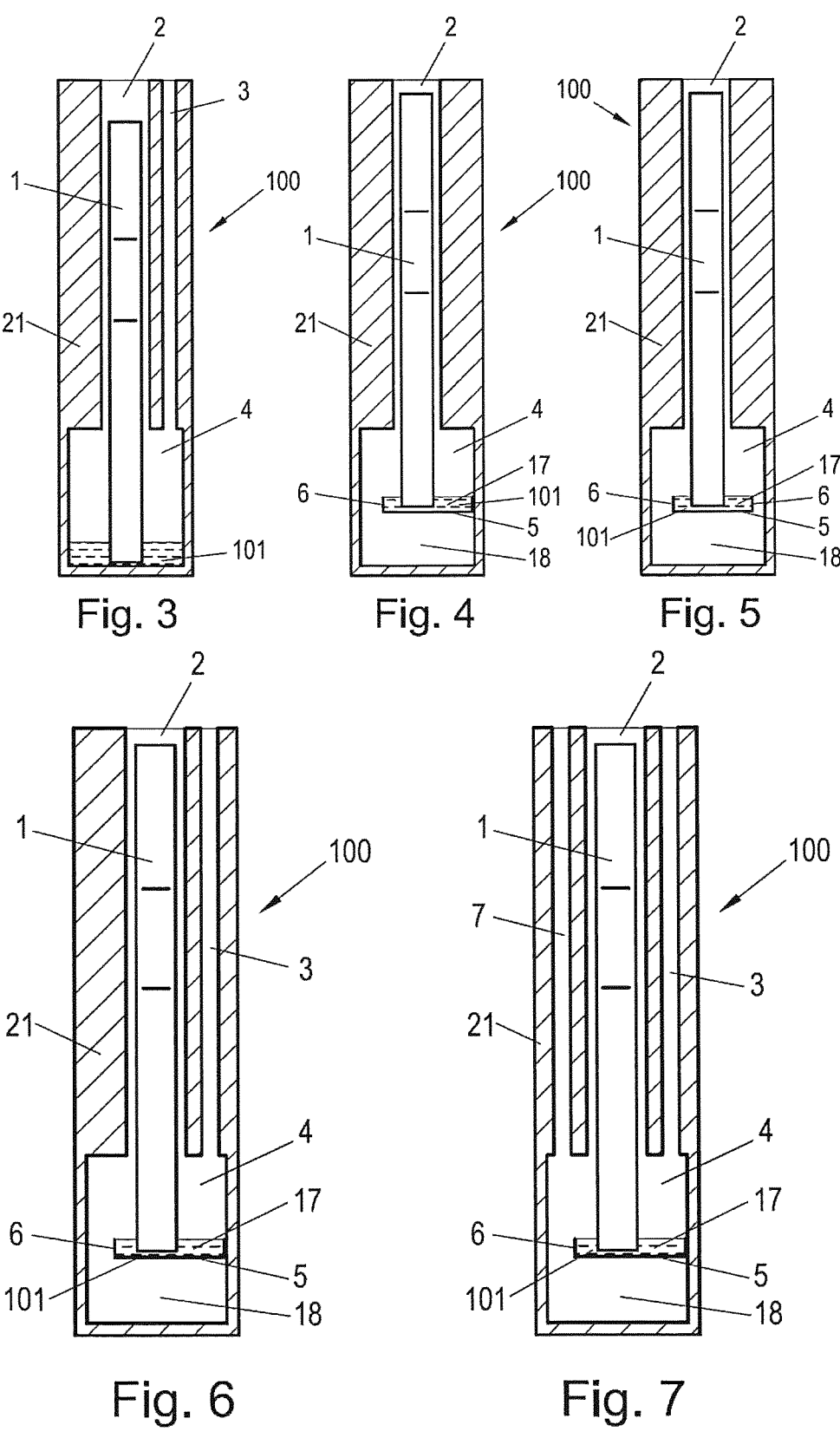
FIG. 3 is a cross-section front view drawing of a lateral flow test strip in a strip holder comprising a strip receiving channel and a fluid receiving channel and a fluid reservoir.
FIG. 4 is a cross-section front view drawing of a strip holder comprising a strip supporting structure with a weir structure.
FIG. 5 is a cross-section front view drawing of an alternative embodiment of a strip supporting structure having two weir structures.
FIG. 6 is a cross-section front view drawing of a strip holder comprising a strip receiving channel and a fluid receiving channel and a strip supporting structure with a weir structure.
FIG. 7 is a cross-section front view drawing of a strip holder comprising a ventilation channel.

FIG. 3 is a frontal cross-section view of a strip holder 100, comprising a channel, which serves as a strip receiving channel 2 and a second channel which serves as a fluid receiving channel 3, wherein the strip receiving channel 2 and the fluid receiving channel 3 are provided in a parallel orientation to one another. The cross-section shown in FIG. 3 further shows a lateral flow test strip 1 contacting a fluid 101, contained in a fluid reservoir 4. Channels and fluid reservoir are formed by wall structures 21 which connect the strip holder front side 9 with the back side 11. When a strip holder 100 as shown in FIG. 3 is provided with an essentially flat back side 11 that is thermally conductive according to the present invention, such a strip holder can be contacted with a heating/cooling element to achieve efficient temperature transfer from the heating/cooling element via the back side 11 to the content of the strip holder 100, thus allowing a detection of analytes at an operator-controlled temperature.

FIG. 4 is a frontal cross-section view of another embodiment of a strip holder 100, comprising a strip receiving channel 2, which serves also as fluid receiving channel, and in addition comprising a strip supporting structure 5 with a weir structure 6. This strip supporting structure 5 with a weir structure 6 can e.g. be attached to one of wall structures 21 of the fluid reservoir 4. The sub-reservoir 17 formed by this strip supporting structure 5 with a weir structure 6 partly separates the fluid reservoir 4 and defines a first sub-reservoir 17 within the fluid reservoir 4. Underneath the first sub-reservoir 17, is a second sub-reservoir 18. FIG. 5 is a cross-section view of a front view of a strip holder, wherein a strip supporting structure 5 with two weir structures 6 is not attached to one of the wall structures 21 of the fluid reservoir 4, but to the front side 9 and the back side 11 of the strip holder 100. A strip holder 100 comprising a strip supporting structure 5 with a weir structure 6 can be used to avoid strip drowning by accidental addition of excess liquid. Added liquid will first fill up the first sub-reservoir 17 formed by the strip supporting structure 5 with at least one weir structure 6, and only when the maximum volume of this first sub-reservoir 17 is reached, excess liquid will flow over the weir structure into the second sub-reservoir 18, thus avoiding drowning of the lateral flow test strip 1 standing in the first sub-reservoir 17.

Referring to the views shown in FIGS. 4-5, the strip receiving channel 2 and the fluid receiving channel are realized by the same channel. In such embodiments, the liquid to be analyzed is introduced into the strip holder 100 via the same channel 2 which is used to introduce the lateral flow test strip 1 into the strip holder 100.

Referring to FIGS. 3, 6-10, the strip receiving channel 2 and the fluid receiving channel 3 are separate channels. By separating the strip receiving channel 2 and the fluid receiving channel 3, the risk of premature wetting of the lateral flow test strip 1 can be avoided and assay handling can be performed more conveniently.

Figures 8, 9, 10, 11, 12, 13:
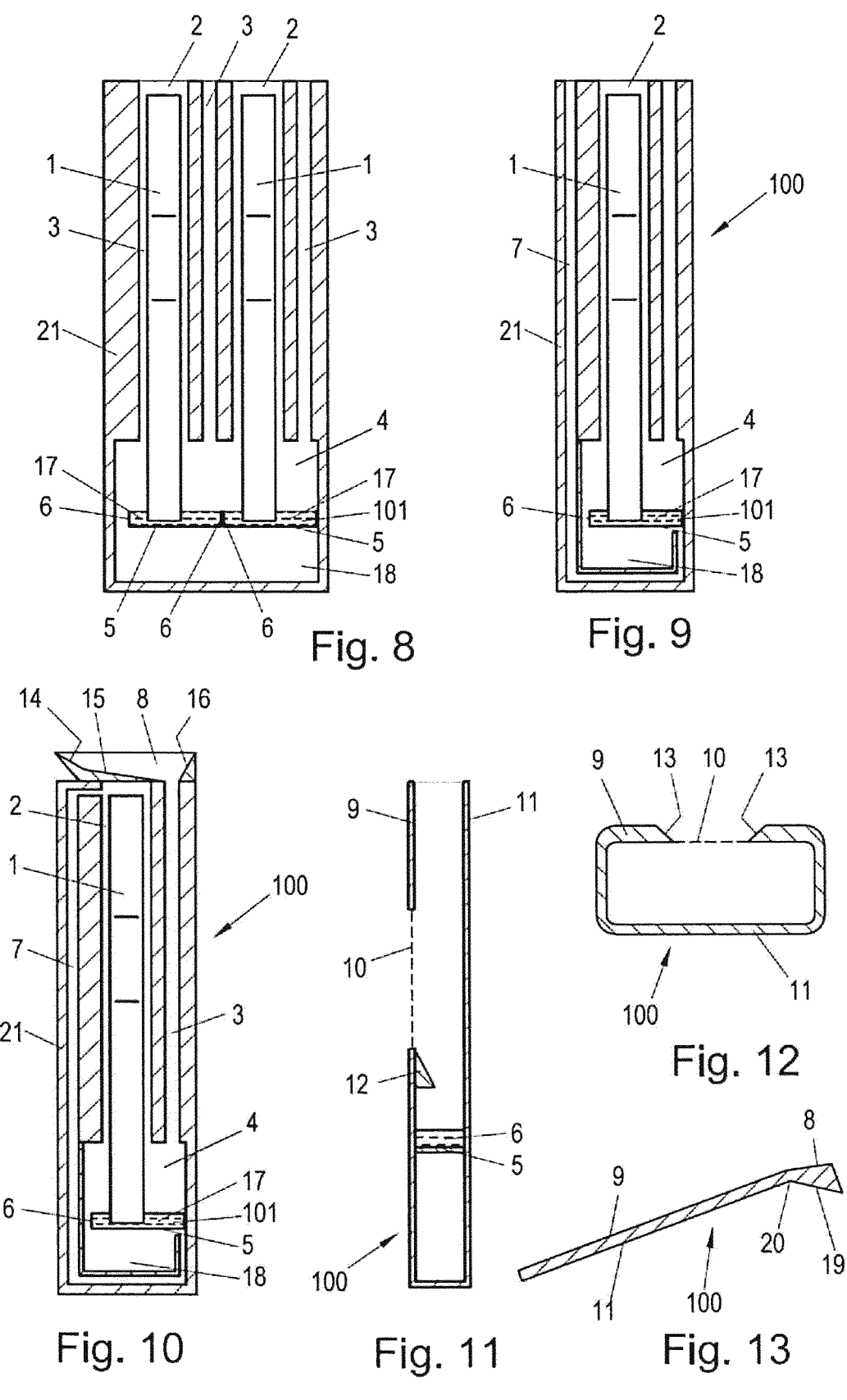
FIG. 8 is a cross-section front view drawing of a strip holder comprising two strip receiving channels and two separate fluid receiving channels and two strip supporting structures with weir structures.
FIG. 9 is a cross-section front view drawing of a strip holder comprising a ventilation channel, wherein the ventilation channel partly surrounds the fluid reservoir.
FIG. 10 is a cross-section front view drawing of a strip holder comprising a funnel.
FIG. 11 is a cross-sectional lateral view of a strip holder with a front side having an inspection window and a back side comprising a wedge-shaped element, a strip supporting structure and a weir structure.
FIG. 12 is a cross-sectional transversal view of a strip holder with a front side having an inspection window with beveled lateral walls.
FIG. 13 is a side view of a strip holder having a funnel.

Referring to FIGS. 7, 9-10 an additional ventilation channel 7 is shown. In FIGS. 9-10, the ventilation channel 7 partially surrounds the fluid reservoir 4. The presence of a ventilation channel allows avoidance of back pressure build-up in the strip holder 100. By providing the ventilation channel 7 in a way that it at least partially surrounds the fluid reservoir 4, the risk of blocking the ventilation channel 7 by spilling of liquid into the ventilation channel 7 can be reduced.

FIG. 8 is a frontal cross-section view of an embodiment of a strip holder 100 according to the present invention, wherein two lateral flow assay strips 1 can be used in the same strip holder 100. It is apparent to a person skilled in the art, that also strip holders can be provided, which allow processing of three or even more lateral flow assay strips. Also such strip holders are encompassed by the present invention. The view of FIG. 8 shows a strip holder comprising two strip receiving channels 2, two fluid receiving channels 3, two separate strip supporting structures 5 with weir structures 6. Instead of having two separate strip supporting structures 5 with weir structures 6, it would also be possible to provide a single strip supporting structure with at least one weir structure, which supports two or more lateral flow test strips.

FIG. 10 is a frontal cross-section view showing a strip holder 100 comprising a funnel 8. Hereby, introduction of a fluid into the strip holder 100 can be achieved most conveniently via this funnel 8. As indicated in FIG. 10, by providing a funnel 8 with at least two differently beveled inner surfaces 14, 15 and 16, it is possible to guide the liquid introduced into the funnel 8 to the fluid receiving channel 3, independent from the location at which the liquid is introduced into the funnel 8.

FIG. 11 is a lateral cross-section view of a strip holder 100 with a front side 9 having an inspection window 10 and a back side 11, comprising a wedge-shaped element 12, a strip supporting structure 5 and a weir structure 6. The inspection window 10 is indicated as dashed line. The wedge-shaped element 12 inhibits insertion of a typical lateral flow test strip into the strip holder 100 in the wrong orientation on the one hand, and applies pressure on a correctly inserted lateral flow test strip to push the strip against the back side 11 of the strip holder 100.

Hereby, a temperature-isolating air gap between the test strip and the back side 11 is minimized, thus achieving ideal temperature transfer from an external heating/cooling element via the back side 11 of the strip holder 100 onto the test strip.

FIG. 12 is a horizontal cross-section view of a strip holder 100 with a back side 11 and a front side 9 having an inspection window 10, wherein the lateral walls 13 of the inspection window 10 are beveled. By providing an inspection window 10 having beveled lateral walls 13, imaging quality can be maximized by avoiding the casting of shadows onto the lateral flow strip by non-beveled lateral walls. As seen in FIG. 12, the back side 11 can be made of the same material as other components of the strip holder, such as the front side 9. It is however apparent that the back side 11 may also be made of a different material than one or more of the other components or structural elements of the strip holder, as disclosed herein.

FIG. 13 is a side view of a strip holder 100 with a back side 11 and a front side 9 and a funnel 8, wherein an outside surface of the funnel 19 is inclined at a different angle than the outside surface of the back side 11. In this example, the angle 20 between the outside surface of the funnel 19 and the outside surface of the back side 11 is approximately 33°. By providing such a strip holder, the angle formed by the outside surface of the funnel 19 and the outside surface of the back side 11 defines a stop which limits the insertion depth of the strip holder into an evaluation apparatus.

EXAMPLES

Example 1—Avoidance of Strip Drowning and Strip Holder Flooding

To avoid the undesirable effect of strip drowning upon undue addition of excess fluid, a strip holder was tested consisting of a housing with a front side comprising an inspection window and a back side, wherein the housing comprised one strip receiving channel and one separate fluid receiving channel, one fluid reservoir and one ventilation channel, wherein the strip receiving channel and the fluid receiving channel were in fluid connection with the fluid reservoir, and wherein the fluid reservoir was partly separated into a first and a second sub-reservoir by a strip supporting structure comprising a weir structure below the strip receiving channel and the fluid receiving channel (FIG. 7). The strip supporting structure was provided to form a first sub-reservoir, defining a nominal geometrical volume of 250 μL, defined by the strip supporting structure orthogonal to the strip receiving channel and the fluid receiving channel, by the back side and the front side of the housing, the lateral wall of the housing and the weir structure. Excess liquid should overflow via the weir structure into the second sub-reservoir below the strip supporting structure, thus avoiding drowning of a strip standing in the strip receiving channel on the strip supporting structure.

Different volumes of aqueous liquid were introduced via the fluid receiving channel into the fluid reservoir, first reaching the first sub-reservoir and—in case of excess volume—overflowing into the second sub-reservoir. The different volumes added and the approximate volumes retained in the first sub-reservoir are shown in Table 1 and illustrated in FIG. 1. It could hereby be demonstrated that the described strip supporting structure was functional and well-suited to deal with excess volumes that might be added by mistake.

TABLE 1

Volumes added into the strip holder, volumes retained in the first
sub-reservoir, overflow volumes in the second sub-reservoir.

| Volume added μL | Volume retained μL | Volume overflow μL |
|---|---|---|
| 100 | 100 | — |
| 150 | 150 | — |
| 200 | 200 | — |
| 250 | 250 | — |
| 300 | 300 | — |
| 350 | 350 | — |
| 400 | 150 | 250 |
| 500 | 150 | 350 |

Example 2—Evaluation of the Influence of
Ambient Temperature

To evaluate the influence of non-controlled ambient temperature, an aqueous solution containing a known concentration of 0.50 ppm of fumonisin B1 was measured in standard LFD assays at three different temperatures: at optimal temperature, 5° C. below the optimal temperature, and 5° C. above the optimal temperature. The fumonisin B1 concentration determined at optimal temperature was 0.49 ppm, the concentration determined 5° C. below the optimal temperature was 0.64 ppm, and the concentration determined 5° C. above the optimal temperature was 0.37 ppm. These results illustrate the importance of controlling the temperature at which an LFD assay is performed to maximize reproducibility and accuracy. When using a strip holder as described herein, such deviations can be avoided entirely by allowing for a control of the temperature at which the assay reaction is performed.

Example 3—Determination of Specific Heat
Transfer Indices

To measure the heat transfer behavior for different strip holder architectures or different strip holder back sides, a common laboratory hotplate (e.g. RCT basic, IKA) was set at 45° C. The strip holder to be measured was fitted with a temperature probe (e.g. Traceable Digital Thermometer, VWR) directly in contact with the inside of the back side at approximately the same height, as the test area of a test strip would sit. The strip holder was then fixed flat onto the hot plate with tape to ensure a close contact, while probe temperature, ambient temperature and incubation time were recorded. Before each new experiment, the temperature probe was allowed to cool down to room temperature, i.e. a temperature between 18° C. and 25° C.

As examples, metal foils as well as plastic foils were tested as strip holder back sides at different thicknesses. Aluminum foils were described to have a thickness of either 9 μm, 40 μm, 125 μm, 0.5 mm, 1 mm or 1.5 mm. Copper as well as silver foils were described to have a thickness of either 1 μm, 50 μm or 1 mm. Zinc foils were described to have a thickness of either 35 μm or 0.5 mm. Foils made of polyethylene, polyvinylchloride, polypropylene, polyester, polycarbonate, polystyrene or acrylonitrile butadiene styrene (ABS) were described to have a thickness of either 8 μm, 40 μm, 0.1 mm, 0.5 mm or 1 mm. The nominal thermal conductivity parameter of aluminum is in the range of approximately 200 W/(m*K), of copper approximately 275 W/(m*K), of silver approximately 430 W/(m*K) and of zinc approximately 110 W/(m*K). The nominal thermal conductivity parameters of plastics such as polyethylene, polypropylene, polyvinylchloride, polystyrene, polyester, polycarbonate, ABS or ABS-like material are considerably lower than of metal foils, at approximately 0.15-0.5 W/(m*K). In detail, data of three different back sides, A, B and C, is exemplarily shown: A back side A was "ThermaSeal RTS™ Sealing Film" purchased from Sigma-Aldrich Handels GmbH. This polyethylene-based film is described as 50 μm thick polyolefin with 50 μm inert encapsulated silicone adhesive. A back side B was "AlumaSeal® II Seal" purchased from Sigma-Aldrich Handels GmbH. This film is described as a 38 μm non-permeable soft aluminum foil. A back side C was a 0.5 mm acrylonitrile butadiene styrene (ABS)-like polymer foil. The recorded data for back sides A, B and C is exemplarily shown in FIG. 2.

To calculate the specific heat transfer indices for the strip holder back sides, the time in seconds required to achieve a temperature transfer of 10° C. from 25° C. to 35° C. from the outside of the back side of a strip holder housing to the inside of the back side of the strip holder housing was measured. For a strip holder with back side A, the time was 6.9 s. For a strip holder with back side B, the time was 5.7 s. For a strip holder with back side C, the time was 12 s. The specific heat transfer indices were determined by calculating the reciprocal of the times measured. The specific heat transfer index for a strip holder with back side A was determined to be $0.145 \text{ s}^{-1}$. The specific heat transfer index for a strip holder with back side B was determined to be $0.175 \text{ s}^{-1}$. And the specific heat transfer index for a strip holder with back side C was determined to be $0.083 \text{ s}^{-1}$. Ultimately, the time required to achieve a temperature transfer of 10° C. from 25° C. to 35° C. from the outside of the back side of a strip holder housing to the inside of the back side of the strip holder housing did not exceed 60 s with any of the tested back sides. In other words, the specific heat transfer index of these strip holder back sides was at least $0.0167 \text{ s}^{-1}$. Most surprisingly, it became thus apparent that not only materials having a high nominal thermal conductivity parameter such as silver (430 W/(m*K)), but also synthetic materials and plastics having a relatively low nominal thermal conductivity parameter (0.15-0.5 W/(m*K)) can be a thermally conductive back side according to the present invention and can thus be suitable as back sides of a strip holder according to the present invention.

The invention claimed is:

1. A strip holder comprising:

a housing which includes a front side, a back side, at least one strip receiving channel, at least one fluid receiving channel, and at least one fluid reservoir, wherein the at least one strip receiving channel and the at least one fluid receiving channel are in fluid connection with the at least one fluid reservoir; and wherein the front side of the housing is made of a solid material and comprises at least one inspection window; and wherein the housing further includes at least one strip supporting structure which partly separates the at least one fluid reservoir, wherein the at least one strip supporting structure comprises at least one weir structure defining a sub-reservoir capable of holding a predefined fluid volume, and wherein the at least one strip supporting structure is provided below the at least one strip receiving channel and the at least one fluid receiving channel; and wherein the at least one strip supporting structure is provided in orthogonal orientation to the at least one strip receiving channel and the at least one fluid receiving channel.

2. The strip holder according to claim 1, wherein the back side of the housing is an essentially flat thermally conductive surface.

3. The strip Strip-holder according to claim 1, wherein the housing further comprises:

a ventilation channel which defines ventilation channel comprises first and second openings, wherein the first opening is provided at the at least one fluid reservoir, and the a second opening is provided at a level above the at least one fluid reservoir.

4. The strip holder according to claim 3, wherein the at least one strip receiving channel includes an insertion opening, and wherein the second opening is provided at a level of the insertion opening.

5. The strip holder according to claim 3, wherein the ventilation channel at least partly surrounds the at least one fluid reservoir.

6. The strip holder according to claim 1, wherein the front side of the housing, the at least one strip receiving channel, the at least one fluid receiving channel, the at least one fluid reservoir, and the at least one ventilation channel are provided as a single piece.

7. The strip holder according to claim 1, wherein the strip holder housing is provided as a single piece.

8. The strip holder according to claim 1, wherein the strip receiving channel further comprises at least one wedge-shaped element which is provided on an inside of the front side.

9. The strip holder according to claim 1, wherein the the at least one inspection window of the at least one strip receiving channel includes lateral walls that are beveled.

10. The strip holder according to claim 1, wherein the at least one fluid receiving channel includes at least one funnel at an opening of the at least one fluid receiving channel directed to the outside.

11. The strip holder according to claim 10, wherein an outside surface of the at least one funnel is inclined at a different angle than an outside surface of the back side of the housing, and wherein the outside surface of the at least one funnel defines an insertion depth of the strip holder into an evaluation apparatus.

12. The strip holder according to claim 1, wherein the back side of the housing is thermally conductive with a specific heat transfer index of at least $0.0167 \text{ s}^{-1}$.

13. The strip holder according to claim 1, wherein the predefined fluid volume of the sub-reservoir is 50 to 5000 µL.

14. The strip holder according to claim 1, wherein the predefined fluid volume of the sub-reservoir is 100 to 300 µL.

15. The strip holder according to claim 1, wherein the predefined fluid volume of the sub-reservoir is 150 to 250 µL.

16. A method for performing a lateral flow assay at an operator defined temperature in an evaluation apparatus comprising a heating and/or cooling module, wherein the lateral flow assay comprises the steps of:

(i) providing the strip holder according to claim 1;

(ii) setting the heating and/or cooling module to a temperature at which the lateral flow assay shall be conducted;

(iii) inserting a lateral flow test strip into the strip holder;

(iv) inserting the strip holder into the evaluation apparatus, wherein the back side of the strip holder is brought into contact with the heating and/or cooling module;

(v) adding a fluid comprising an analyte to be detected into the strip holder; and (vi) incubating the strip holder containing the lateral flow test strip and the fluid for a predefined time.

17. The method according to claim 16, wherein the predefined time of step (vi) is at least one second.

18. The method according to claim 16, wherein the predefined time of step (vi) is at least three seconds.

19. The method according to claim 16, wherein the predefined time of step (vi) is at least five seconds.

20. A kit comprising the strip holder according to claim 1, at least one lateral flow assay strip and an evaluation apparatus, wherein the evaluation apparatus is capable of receiving the at least one strip holder and wherein the evaluation apparatus comprises a temperature control element.

\* \* \* \* \*